United States Patent [19]

Corbett et al.

[11] 4,189,538

[45] Feb. 19, 1980

[54] METHOD FOR GROWING PSEUDOMYCELIAL YEASTS AND REDUCING BACTERIAL CONTAMINATION IN A YEAST FERMENTATION PROCESS

[75] Inventors: Constance R. Corbett, White Plains, N.Y.; John A. Ridgway, Jr., LaPorte, Ind.; Helen D. Haller, Ithaca, N.Y.

[73] Assignee: Standard Oil Company (Indiana), Chicago, Ill.

[21] Appl. No.: 917,896

[22] Filed: Jun. 22, 1978

Related U.S. Application Data

[63] Continuation-in-part of Ser. No. 755,865, Dec. 30, 1976, abandoned.

[51] Int. Cl.$^2$ ............................................... C12B 1/00
[52] U.S. Cl. ................................ 435/247; 435/255; 435/256; 435/261; 435/804; 435/813
[58] Field of Search ................. 195/28 R, 49, 82, 107, 195/112, 115, 121, 108, 109; 426/60, 62

[56] References Cited

U.S. PATENT DOCUMENTS

| | | | |
|---|---|---|---|
| 3,616,260 | 10/1971 | Muller | 195/107 |
| 3,868,305 | 2/1975 | Masuda et al. | 195/49 |
| 3,929,578 | 12/1975 | Urakami | 195/82 |
| 3,982,998 | 9/1976 | Hitzman et al. | 195/115 |

OTHER PUBLICATIONS

Lodder "The Yeasts" North Holland Publishing Co., 1970, pp. 1064–1065.

*Primary Examiner*—R. B. Penland
*Attorney, Agent, or Firm*—Gregory E. Croft; Arthur G. Gilkes; William T. McClain

[57] ABSTRACT

Growth of pseudomycelial yeasts and removal of bacterial contamination in conventional fermentation processes are accomplished by withdrawing product as a foam from the fermentor.

12 Claims, No Drawings

METHOD FOR GROWING PSEUDOMYCELIAL YEASTS AND REDUCING BACTERIAL CONTAMINATION IN A YEAST FERMENTATION PROCESS

This application is a continuation-in-part of copending application Ser. No. 755,865 filed Dec. 30, 1976 now abandoned.

BACKGROUND OF THE INVENTION

1. Field of the Invention

This invention relates to fermentation processes for the production of food yeasts. More particularly, it relates to fermentation processes for the production of pseudomycelial yeasts.

2. Description of the Prior Art

In recent years, much attention has been directed toward the development of new sources of protein which can be incorporated in foods or food additives suitable for human consumption. Rapid increases in world population have made the continued dependence on traditional sources of protein highly impractical. Moreover, the supply of protein from typical sources of protein, such as animal meat and certain vegetables, is inadequate to provide balanced diets sufficient to satisfy the needs of humans throughout the world.

One possible solution to the problem of supplying the ever-increasing need for food protein is provided by processes for the bio-synthetic manufacture of protein through the growth of microorganisms on hydrocarbons or other substrates. It is known, for example, that microorganisms such as bacteria, fungi, and yeast, which are grown by single-cell reproduction, contain high proportions of proteins and can be utilized directly in foods as a whole cell material or can be treated to recover protein concentrate and protein isolate.

With the development of successful processes for the fermentation production of protein-containing microorganisms (sometimes referred to herein as single-cell proteins), a need has developed for methods of texturizing such single-cell protein materials in a manner sufficient to render them suitable alone or in combination with plant and/or animal proteins for use in food products.

Generally, single-cell proteins are initially produced as an aqueous slurry and then subsequently converted into dry powder form, generally having a particle size of about 325 mesh. This dry powder, similar in appearance and feel to flour, lacks the texture and food-like sensation in the mouth necessary to make an attractive food and often imparts a mushy texture to the food into which it is incorporated. Moreover, when placed in water, agglomerated particles of single-cell protein rapidly revert back to single-cell form.

One solution for improving the texture of the yeast in food products is to produce a yeast product having a larger particle size. A type of yeast which meets this requirement is pseudomycelial yeast, which is a multi-cell variant of the more common single-cell variety. The pseudomycelial yeasts are actually clusters of single-cell yeasts which may contain hundreds of individual cells, thus having a particle size much greater than the typical single-cell yeast. These larger pseudomycelial yeasts have superior texturization properties than their single-cell counterparts and also are easier to separate and recover from the fermentation broth because of their greater mass.

Accordingly, it is an object of this invention to provide a process for selectively producing a yeast product containing the pseudomycelial variant of *Candida utilis*.

A further object of this invention is to provide a process which encourages pseudomycelial cell development and reduces bacterial contamination. These and other objects of this invention will become apparent upon further reading of this specification.

SUMMARY OF THE INVENTION

In one aspect, the invention resides in a continuous fermentation process wherein a substrate, nutrients, and an oxygen-containing gas are fed into a continuous zone of agitated liquid fermentation in which foaming occurs, the improvement comprising continually withdrawing foam at a rate sufficient to reduce the concentrations of bacterial contaminants and single-cell yeasts and to promote growth of pseudomycelial yeasts. The yeast cells residing in the withdrawn foam are subsequently recovered and dried in any suitable manner.

More particularly, the invention resides in a continuous yeast fermentation process for producing a pseudomycelial variant of *Candida utilis*. The process comprises (a) adding an ethanol substrate, nutrients, and air to a continuous zone of agitated fermentation in which foaming occurs, said zone of agitated fermentation being maintained under super-atmospheric pressure at a temperature of from about 80 to about 98° F., a pH of from about 4 to 5, and having a yeast cell concentration of from about 0.5 to about 3.5 weight percent; and (b) continuously withdrawing the foam at a rate sufficient to promote pseudomycelial growth in the liquid phase or reduce bacterial contamination. The withdrawn foam contains a mixture of yeasts which can be easily separated from the liquid phase and dried in a conventional manner. The super-atmospheric pressure in the fermentor serves only to help prevent contaminants from entering the system. Pressures from about 3 to about 20 psig are suitable.

Removal and subsequent recovery of the pseudomycelial yeast-containing fermentation product can essentially be accomplished by either of two methods. In one method the product stream can consist solely of withdrawn foam, in which case the recovered foam is broken and the yeasts are recovered, as by centrifugation and spray-drying. Alternatively, the product stream can consist of both withdrawn foam and withdrawn liquid, in which case the withdrawn foam and liquid streams can be combined and the yeast cells recovered in a suitable manner. In either case, the resulting yeast product will contain single-cell yeasts in addition to the desired pseudomycelial variant, although the relative amount of each will be greatly influenced by the percentage of product withdrawn as a foam. The pseudomycelial cells may optionally be separated from the single cells if desired, but such separation is not necessary to obtain an improvement in texturization over the single-cell product.

Alhough the process of this invention is particularly applicable to *Candida utilis*, it can also be applied to other yeasts, including *Saccharomyces cerevisiae*, *Saccharomyces fragilis*, and *Saccharomyces carlsbergensis*.

DESCRIPTION OF THE PEFERRED EMBODIMENT

As in a typical continuous fermentation system, a substrate, nutrients, and an oxygen-containing gas, such as air, were fed to an agitated fermentor at a constant rate. The agitation improves the gas-liquid mass transfer and maintains a uniform cell suspension. The pH of the fermentor contents was controlled on signal by the addition of ammonia. The temperature within the fermentor was controlled by the continuous circulation of cold water through cooling baffles. The fermentor contents were continuously withdrawn at a rate equal to the rate of substrate and nutrient addition and were deposited in cooled product tanks for temporary holding. From there, the cooled product was centrifuged to separate and recover the cells, which were then dried and stored.

In the usual continuous fermentation, the fermentor contents consist of a major quantity of a predominantly liquid phase and a minor amount of a predominantly gas phase (foam layer). The foam layer is in equilibrium with the liquid phase and generally has no significant effect on the course of the fermentation. The fermentation product, which can be defined as the yeast cells produced in the fermentor, is always withdrawn from the liquid phase (middle draw-off), which assures that the product will be of the same composition as the bulk of the fermentor contents. If two competing species are present in such a system, the faster growing of the two will soon predominate. When the two competing species are of the single-cell and pseudomycelial type, for example, the single-cell type soon predominates. Also, in such typical fermentations antifoam additives are generally used to suppress foaming caused by the agitation. In such operations, any excess foam still formed is removed from the fermentor by a trap and discarded, but in amounts insufficient to reverse the dominance of the single-cell variant in the liquid phase.

Most unexpectedly, it has now been discovered that simply by changing the location of the draw-point from below the liquid surface to a point above the liquid surface (top draw-off), selective growth of predominantly pseudomycelial cells and preferential removal of bacterial contaminants and single-cells is achieved. Apparently, by introducing into such a system a degree of selectively in harvesting such that the ratio of the two organisms in the product stream differs from that in the bulk of the fermentor, the result of the growth rate competition is effected. We have discovered that the ratio of single-cell to pseudomycelial variants is higher in the fermentor foam phase than in the liquid phase. Also, the concentration of bacterial contaminants in the foam phase is higher than in the liquid phase. Hence when the foam is harvested, along with any quantity of liquid necessary to maintain a viable continuous process, the ratio of single-cell to pseudomycelial cells in the product is still greater than in the bulk liquid phase of the fermentor. We have found that this ratio is sufficient to increase the single-cell harvest rate relative to the pseudomycelial cell rate to that point where the growth rate competition is upset and the fermentor contents is gradually converted to predominantly pseudomycelial cells. The advantages of such a process include the superiority of the pseudomycelial cell yeast over the single-cell yeast in texturization, ease of separation and recovery of the product, and reduction of bacterial contamination. The pseudomycelial form can be induced by mutation or adaption, or can be purposely added to the system. It must be pointed out that even if the pseudomycelial variant were not produced, the advantage of reduced bacterial contamination would still be a substantial benefit from practicing this invention.

During our experimentation, the operating conditions of the fermentor were as follows using the top draw-off procedure:

| | |
|---|---|
| Type of yeast: | *Candida utilis* |
| Substrate | Ethanol |
| Nutrients | P, K, Mg, trace elements |
| Temperature: | 85.5°–86° F. |
| Pressure | 8.0–8.5 psig |
| Stirrer speed: | 800 rpm |
| Fermentor level: | 16 liters |
| Air rate: | 262 liters/hour/liter fermentor liquid |
| pH: | 4.0 |
| Cell concentration: | 0.66–0.72 weight per cent |

The fermentor was initially inoculated with the standard single-cell type *Candida utilis* yeasts. After seven days of continuous operation under the above conditions, definite pseudomycelial morphology appeared in microscopic examinations of the fermentor contents. Prior to the appearance of the pseudomycelial form, the ratio of single cell concentration in the effluent foam to that in the fermentor liquid phase was about 5:1, indicating the tendency of the single-cell type yeast to preferentially reside in the foam. After the morphological change occurred, this same ratio was reduced to 1:2, indicating the stronger tendency for the heavier pseudomycelial yeasts to reside in the liquid (differential sedimentation). This data showed that removal of foam (foam fractionation) preferentially removes the single-cell yeasts and therefore promotes pseudomycelial growth.

To further test the discovery, the draw-off point in the fermentor was changed to the middle (below the liquid surface), and a small (about 10%) inoculum of fresh single-cell *Candida utilis* yeasts was charged to the fermentor, along with the addition of an antifoaming agent at the top of the fermentor. Two important changes subsequently occurred. First, there was an equlization of dry weights of cells in the effluent foam and the fermentor, indicating an increase in the single-cell concentration in the foam portion. Second, a decrease in the concentration of the pseudomycelial cells in the fermentor suspension was accompanied by approximately a 50% increase in the concentration of single-cells and bacteria. This is interpreted as meaning that in the absence of top draw-off, the faster growing single-cells and bacteria predominate.

In addition, another run was made in which the middle draw-off procedure was used for the entire run. After approximately one month of operation, no significant chain or pseudomycelial cell formation was detected.

These results show that growth of pseudomycelial variants and a reduction of bacterial contamination can be accomplished by using a top draw-off procedure and that the phenomena can be reversed by changing the draw-off location to the middle.

As previously indicated, in a continuous process according to this invention it is not necessary that 100% of the fermentor product be withdrawn as a foam. Because the degree of foam formation will decrease as the concentration of pseudomycelial cells increase, the rate of foam removal may become undesirably low for a viable continuous process. Therefore, it may be desirable to additionally withdraw a portion of the product from the liquid phase of the fermentor. It must be appreciated that such an operation will serve to shift the equilibrium more in favor of the single-cell variant than if only foam were withdrawn, but such harvesting procedure can be used and still obtain the benefits of this invention, i.e., an increase in pseudomycelial cell yield and reduction in bacterial contamination.

It will be obvious to those skilled in the art that many variations can be made from the preferred embodiment, shown for purposes of illustration, without departing from the scope of this invention defined by the following claims.

We claim:

1. In a continuous yeast fermentation process wherein a substrate, nutrients, and an oxygen-containing gas are fed into a fermenter containing an agitated liquid fermentation medium in which foaming of the contents occurs and wherein said yeast forms a pseudomycelial variant, the improvement comprising continually withdrawing foam from the top of the fermenter at a rate sufficient to reduce the concentration of single-cell yeast which preferentially reside therein in order to promote growth of the pseudomycelial variant in the liquid phase and recovering cells enriched in said pseudomycelial variant from said liquid phase.

2. The process of claim 1 wherein cells enriched in said pseudomycelial variant are withdrawn only as a foam.

3. The process of claim 1 wherein the yeast is selected from the group consisting of *Candida utilis, Saccharomyces cerevisiae, Saccharomyces fragilis,* and *Saccharomyces carlsbergensis.*

4. The process of claim 1 wherein the yeast is *Candida utilis.*

5. The process of claim 1 wherein the oxygen-containing gas is air.

6. The process of claim 1 wherein the contents of the continuous zone of agitated fermentation are maintained under super-atmospheric pressure at a temperature of from about 80 to about 98° F., and a pH of from about 4 to about 5.

7. A continuous yeast fermentation process for producing a pseudomycelial variant of *Candida utilis* comprising:
   (a) adding an ethanol substrate, nutrients, and air to a fermenter containing an agitated liquid fermentation medium in which foaming occurs, said fermenter being maintained under super-atmospheric pressure at a temperature of from about 80 to about 98° F., and a pH of from about 4 to about 5, and having a yeast cell concentration of from about 0.5 to about 3.5 weight percent; and
   (b) continuously withdrawing foam from the top of the fermenter at a rate sufficient to reduce the concentration of single-cell yeasts which preferentially reside therein in order to promote the production of the pseudomycelial variant in the liquid phase and recovering cells enriched in said pseudomycelial variant from said liquid phase.

8. The process of claim 7 wherein the continuous zone of agitated fermentation is maintained at a temperature of about 85° F., a pressure of from about 3 to about 20 psig., and a pH of about 4 and having a yeast cell concentration of about 0.7 weight percent.

9. The process of claim 8 wherein the pseudomycelial yeast product is separated and dried.

10. The process of claim 7 wherein cells enriched in said pseudomycelial variant are withdrawn only as a foam.

11. The pseudomycelial yeast product produced by the process of claim 1.

12. The pseudomycelial yeast product produced by the process of claim 7.

* * * * *